United States Patent
Liu et al.

(10) Patent No.: US 7,858,722 B2
(45) Date of Patent: Dec. 28, 2010

(54) PROCESS FOR MAKING AN ACRYLIC MONOMER HAVING ONE OR MORE QUATERNARY AMMONIUM GROUPS AND ITS POLYMERS

(75) Inventors: Leo Zhaoqing Liu, Shanghai (CN); Jon D. Kiplinger, Plainsboro, NJ (US); Douglas Radtke, Hightstown, NJ (US)

(73) Assignee: Rhodia Inc., Cranbury, NJ (US)

( * ) Notice: Subject to any disclaimer, the term of this patent is extended or adjusted under 35 U.S.C. 154(b) by 505 days.

(21) Appl. No.: 12/077,326

(22) Filed: Mar. 19, 2008

(65) Prior Publication Data

US 2008/0234432 A1 Sep. 25, 2008

Related U.S. Application Data

(60) Provisional application No. 60/919,705, filed on Mar. 23, 2007.

(51) Int. Cl.
*C08F 12/28* (2006.01)
(52) U.S. Cl. ............... 526/310; 526/311; 526/312
(58) Field of Classification Search ........ 526/310, 526/311, 312
See application file for complete search history.

(56) References Cited

U.S. PATENT DOCUMENTS

| | | | |
|---|---|---|---|
| 4,387,017 A | 6/1983 | McEntire et al. | |
| 4,495,367 A | 1/1985 | Dammann | |
| 4,973,637 A | 11/1990 | Morgan et al. | |
| 5,115,065 A * | 5/1992 | Ogawa et al. | 526/304 |
| 6,596,261 B1 | 7/2003 | Adjei et al. | |
| 2003/0223951 A1 | 12/2003 | Geary et al. | |

OTHER PUBLICATIONS

Voeffray et al. 193 L-Carnitine. Novel Synthesis and Determination of the Optical Purity, 1987, Helvetica Chimica Acta, vol., pp. 2058-2064, especially p. 2060, Scheme 2, compound 5 to compound 8.

* cited by examiner

*Primary Examiner*—Edward J Cain

(57) ABSTRACT

A method for making a monomer having an ethylenically unsaturated group and two or more quaternary ammonium groups per molecule, comprising:

(a) reacting an excess of a monomeric reactant having at least one ethylenically unsaturated group and at least one tertiary amino group per molecule with a halohydroxyalkyl (trialkyl)quaternary ammonium salt, in an aqueous medium, (b) monitoring the pH of the aqueous medium from at least as early as the time when all reactants have been added to aqueous medium until completion of the reaction, and (c) adjusting the pH of the aqueous medium to and maintaining the pH of the aqueous medium at a value greater than or equal to 9, from the time, after all reactants have been added to aqueous medium, that the reaction mixture exhibits an apparent pH minimum until completion of the reaction.

9 Claims, No Drawings

PROCESS FOR MAKING AN ACRYLIC MONOMER HAVING ONE OR MORE QUATERNARY AMMONIUM GROUPS AND ITS POLYMERS

This application claims the benefit of U.S. Provisional Application No. 60/919,705, filed Mar. 23, 2007.

FIELD OF THE INVENTION

This invention relates to a process for making an acrylic monomer having one or more quaternary ammonium groups and for making polymers from such monomer.

BACKGROUND OF THE INVENTION

Di-quaternary acrylic monomers can be prepared from their tertiary amine by reacting it with (3-chloro-2-hydroxypropyl)trialkylammonium chloride as described in U.S. Pat. No. 4,495,367.

Polymers having monomeric units derived from di-quaternary monomers have found application in water treatment, oil-field, and consumer applications, such as, for example, as demulsifers for bitumen-containing emulsions, as described in U.S. Pat. No. 4,387,017, as hair conditioners, as described in U.S. Patent Application No. 2003/223,951, and as additives in cleaning compositions, as described in U.S. Pat. No. 6,596,261. However, known di-quaternary monomers typically contain residual non-reacted (3-chloro-2-hydroxypropyl)trimethylammonium chloride, as well as non-reacted glycidyltrialkylammonium chloride, a reaction intermediate. These impurities are difficult to separate from the monomers and thus typically end up in the polymers made from such monomers. Both of the chloride impurities are known to be toxic and their presence in such polymer products is undesirable.

SUMMARY OF THE INVENTION

In a first aspect, the present invention is directed to a method for making a monomer having an ethylenically unsaturated group and two or more quaternary ammonium groups per molecule (a "multi-quaternary monomer"), comprising:
(a) reacting an excess of a monomeric reactant having at least one ethylenically unsaturated group and at least one tertiary amino group per molecule with a halohydroxyalkyl(trialkyl)quaternary ammonium salt, in an aqueous medium,
(b) monitoring the pH of the aqueous medium from at least as early as the time when all reactants have been added to aqueous medium until completion of the reaction, and
(c) adjusting the pH of the aqueous medium to and maintaining the pH of the aqueous medium at a value of greater than or equal to 9, from the time, after all reactants have been added to aqueous medium, that the reaction mixture exhibits an apparent pH minimum until completion of the reaction.

In a second aspect, the present invention is directed to a process for making a polymer wherein one or more monomeric units of the polymer each comprise two or more quaternary ammonium groups per monomeric unit, comprising:
(a) making a monomer having an ethylenically unsaturated group and two or more quaternary ammonium groups per molecule by:
(i) reacting an excess of a monomer having at least one ethylenically unsaturated group and at least one tertiary amino group per molecule with a halohydroxyalkyl(trialkyl)quaternary ammonium salt in an aqueous medium,
(ii) monitoring the pH of the aqueous medium from at least as early as the time when all reactants have been added to aqueous medium until completion of the reaction, and
(iii) adjusting the pH of the aqueous medium to and maintaining the pH of the aqueous medium at a value of greater than or equal to 9, from the time after all reactants have been added to aqueous medium, that the reaction mixture exhibits an apparent pH minimum until completion of the reaction, and
(b) polymerizing the monomer formed in step (a) in the presence of a polymerization initiator mixture.

The monomer and the polymer exhibit a reduced level of impurities typically a non-detectable level of unreacted halohydroxyalkyl(trialkyl)quaternary ammonium salt and a non-detectable level of glycidyltrialkylammonium chloride.

DETAILED DESCRIPTION OF INVENTION AND PREFERRED EMBODIMENTS

As used herein, the terminology "$(C_x\text{-}C_y)$" in reference to an organic group, wherein x and y are each integers, indicates that the group may contain from x carbon atoms to y carbon atoms per group.

As used herein, the term "alkyl" means a monovalent saturated straight chain or branched hydrocarbon group, typically a monovalent saturated $(C_1\text{-}C_6)$ hydrocarbon group, such as for example, methyl, ethyl, n-propyl, iso-propyl, n-butyl, sec-butyl, t-butyl, pentyl, or n-hexyl.

As used herein, the term "alkylene" means a bivalent saturated straight chain or branched hydrocarbon group, more typically a divalent saturated $(C_1\text{-}C_6)$ hydrocarbon, such as for example, methylene, dimethylene, and trimethylene.

The aqueous medium comprises water and, optionally, up to about 90 percent by volume of a water miscible organic liquid, such as for example, an alcohol, such as methanol or ethanol.

In one embodiment, the reaction is conducted using a total amount of greater than or equal to about 1.01 moles, more typically, from about 1.01 to about 1.5 moles of the first monomeric reactant per mole of the total amount of halohydroxyalkyl(trialkyl)quaternary ammonium salt.

The reactants may each be introduced to the reaction mixture as one or more discrete portions or as a feed into the reaction mixture over the course of the reaction, or as a combination thereof, for example, as an initial shot of a first portion followed by a feed of the remaining portion.

In one embodiment, the aqueous medium and the total amount of the monomeric reactant are each present in the reactor at the beginning of the reaction and the halohydroxyalkyl(trialkyl)quaternary ammonium salt is fed into the reactor over time.

In one embodiment, the reaction mixture for making the reaction for making the multiquaternary monomer further comprises a polymerization inhibitor, such as one or more hydroquinone compounds to inhibit polymerization of the reactant monomer and/or product monomer during synthesis of the product multiquaternary monomer. Suitable hydroquinones include, for example, hydroquinone and methyl hydroquinone.

In one embodiment, the reaction for making the multiquaternary monomer is conducted with an air sparge to inhibit polymerization of the reactant monomer and/or product monomer during synthesis of the product multiquaternary monomer.

In one embodiment, the reaction of the monomer having at least one ethylenically unsaturated group and the at least one aminoalkyl functional group per molecule with a halohydroxyalkyl(trialkyl)quaternary ammonium salt is conducted within a temperature range of from about 50° C. to about 90° C., more typically from about 55° C. to about 75° C. Typically, the reaction is run for a reaction time of from about 1 to about 8 hours, more typically from about 3 to about 6 hours.

In one embodiment of the method for making a monomer having an ethylenically unsaturated group and two or more quaternary ammonium groups per molecule is made according to Scheme A:

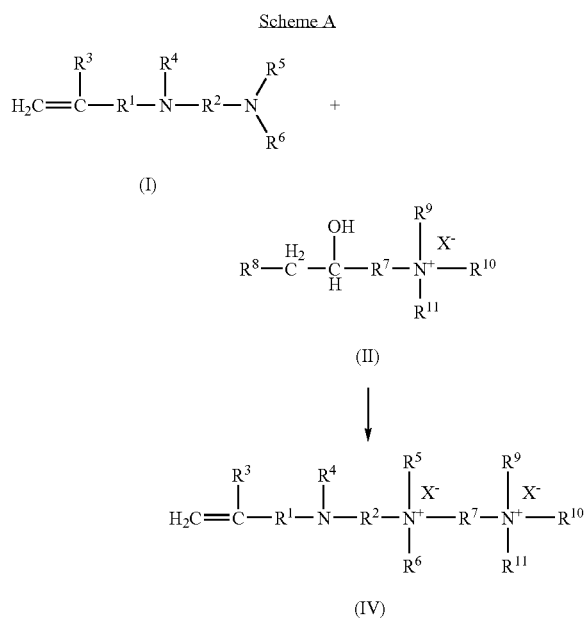

by reacting an excess of a monomer according to structure (I), wherein:
$R^1$ is a divalent organic linking group, more typically carbonyl or alkylene, which may optionally be substituted on one or more carbon atoms or interrupted at one or more sites by heteroatoms,
$R^2$ is alkylene, more typically $(C_2-C_6)$alkylene, which may optionally be substituted on one or more carbon atoms or interrupted at one or more sites by heteroatoms, or a group according to:

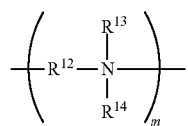

wherein
$R^{12}$ is alkylene, more typically $(C_2-C_6)$alkylene, which may optionally be substituted on one or more carbon atoms or interrupted at one or more sites by heteroatoms,
$R^{13}$ and $R^{14}$ are each independently alkyl, more typically $(C_1-C_6)$alkyl, and
m is an integer of from 1 to 6,
$R^3$ is H or $(C_1-C_6)$alkyl, more typically H or $(C_1-C_2)$alkyl,
$R^4$ is H or $(C_1-C_6)$alkyl, more typically H or $(C_1-C_2)$alkyl,
$R^5$ and $R^6$ are each independently $(C_1-C_6)$alkyl, with a haloalkyl(trialkyl)quaternary ammonium salt according to structure (II), wherein:
$R^7$ is a divalent organic linking group, typically alkylene, and more typically $(C_2-C_6)$alkylene,
$R^8$ is halo, more typically chloro,
$R^9$, $R^{10}$ and $R^{11}$ are each independently alkyl, more typically $(C_1-C_6)$alkyl, and
$X^-$ is an anion, more typically $Cl^-$ to form a monomer (IV) having an ethylenically unsaturated group and two quaternary ammonium groups per molecule, wherein $R^1$, $R^2$, $R^3$, $R^4$, $R^5$, $R^6$, $R^7$, $R^9$, $R^{10}$, and $R^{11}$ are each as described above.

The pH of the aqueous medium is monitored from at least as early as the time when all reactants have been added to aqueous medium until completion of the reaction. At a point after all reactants have been added to aqueous medium, the pH value exhibits an apparent minimum, that is, the pH initially drops, passes through an apparent minimum value, and then begins to increase.

It has been observed that in the absence of the pH adjusting step of the process of the present invention, the rate at which the reaction according to Scheme A proceeds tends to slow markedly after the point that the reaction medium exhibits a pH minimum and to then fail to reach complete conversion of the limiting reactant species.

Once the pH has exhibited an apparent minimum value and has begun to increase, a base is added to the reaction medium to adjust the pH to a value greater than or equal to 9. The upward adjustment of the pH increase the rate of reaction and allows the reaction to keep moving forward to generate product compound (IV), typically to complete conversion of compound (II), the limiting reactant.

In one embodiment, the base is an alkali metal hydroxide, more typically NaOH or KOH, MgOH, quaternary ammonium hydroxide, even more typically, NaOH. Typically, from about 100 parts per million ("ppm") to about 10000 ppm, more typically from about 500 to about 2000 ppm, base are added to the reaction mixture to adjust the pH to a value of greater than or equal to 9.

While not wishing to be bound by theory, it is believed that, in parallel with the reaction according to Scheme A, compound (II) also tends to undergo an internal cyclization reaction to produce an epoxide-functional intermediate according to structure (III):

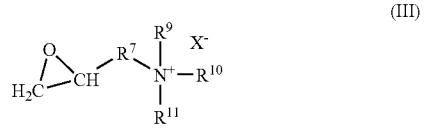

wherein:
$R^7$, $R^9$, $R^{10}$, and $R^{11}$ are each as described above, and that the intermediate (III) then reacts with monomer (I) to form the desired product (IV) and a hydroxyl ion. However, the parallel route to compound (IV) through intermediate compound (III) also generates acid residue which slows the production of compound (IV), to the point of stalling the reaction at less than complete conversion of the reactants. While not wishing to be bound by theory, we believe that the pH adjustment step of the method of the present invention neutralizes the acid residue and overcomes the associated inhibitory effect on the reaction rate.

Suitable polymerization initiators are known and include, for example, compounds which decompose to yield free radical species, such as. azo compounds, peroxides, and persulfates, such as sodium persulfate.

In one embodiment, the polymerization initiator comprises a redox initiator couple comprising sodium persulfate and sodium metabisulfate.

In one embodiment, the polymerization reaction is conducted in an aqueous medium, more typically in water.

In one embodiment, the polymerization reaction is conducted within a temperature range of 25° C. to 150° C., more typically 50° C. to 100° C., for a reaction time of from about 1 to about 20 hours, more typically of from about 3 to about 8 hours.

In one embodiment, the polymerization is conducted under an inert atmosphere, typically, a nitrogen atmosphere.

In one embodiment, a polymer is made according to Scheme B:

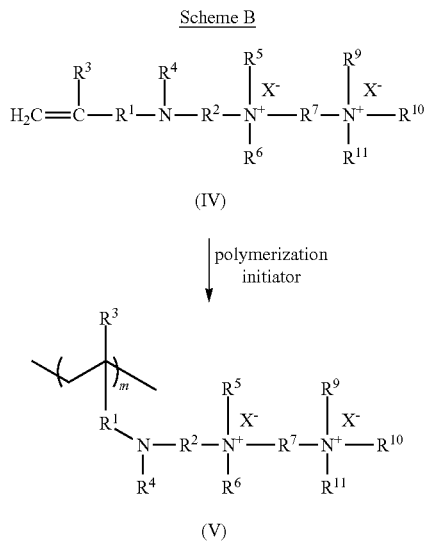

Scheme B by polymerizing a monomer according to structure (IV), wherein $R^1$, $R^2$, $R^3$, $R^4$, $R^5$, $R^6$, $R^7$, $R^9$, $R^{10}$, $R^{11}$ and $X^-$ are each as described above, in the presence of a polymerization initiator to form a homopolymer according to structure (V), wherein $R^1$, $R^2$, $R^3$, $R^4$, $R^5$, $R^6$, $R^7$, $R^9$, $R^{10}$, $R^{11}$, and $X^-$ are each as described above, and m is an integer of from 2 to about 30,000, more typically from 2 to about 4,000.

In another embodiment, a polymer wherein one or more monomeric units of the polymer each comprise two quaternary ammonium groups per monomeric unit is made according to Scheme C:

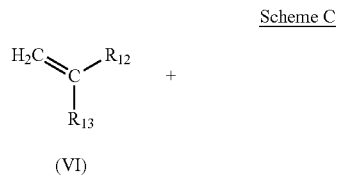

Scheme C

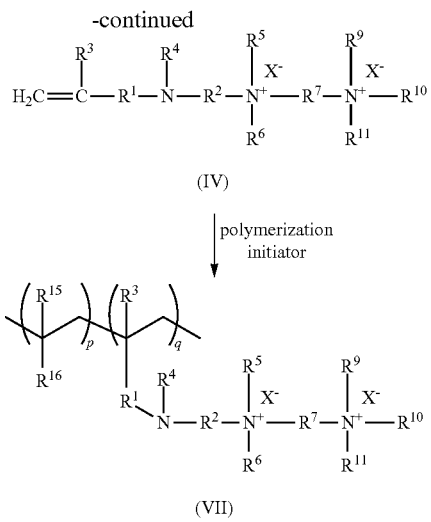

by copolymerizing a monomer according to structure (IV), wherein $R^1$, $R^2$, $R^3$, $R^4$, $R^5$, $R^6$, $R^7$, $R^9$, $R^{10}$, $R^{11}$, and $X^-$ are each as described above, with a comonomer (VI), wherein $R^{15}$ is H or ($C_1$-$C_6$)alkyl, more typically H or $C_1$-$C_2$)alkyl, and $R^{16}$ is hydroxyl, in the presence of a polymerization initiator to form a copolymer according to structure (VII), wherein $R^1$, $R^2$, $R^3$, $R^4$, $R^5$, $R^6$, $R^7$, $R^9$, $R^{10}$, $R^{11}$, $R^{15}$, $R^{16}$, and $X^-$ are each as described above, and p and q are each integers of from 1 to about 100,000, more typically from 1 to about 10,000.

Example 1

A monomer having an ethylenically unsaturated group and two quaternary ammonium groups per molecule is made according to Scheme A-1.

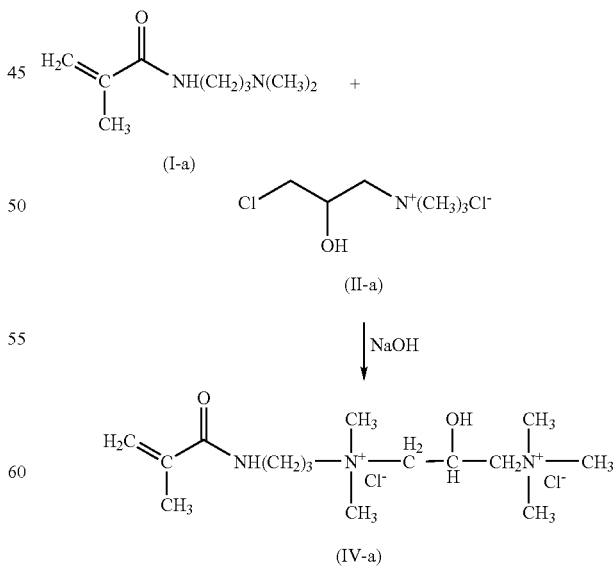

Scheme A-1

57.0 grams dimethylaminopropylmethacryamide (II) was charged to a 500 ml round bottom flask equipped with mechanic stirrer, thermocouple, gas inlet, feeding port and pH probe. The contents of the flask were heated to a temperature in the range of from 62° C. to 63° C. under air sparging. When temperature reached 60° C., a feed of DowQuat 188 (I)) was begun. 93.08 grams of compound (I) diluted in 29.77 grams of distilled water were fed into the flask over 2 hours. The temperature was controlled between 60° C. and 63° C. with cooling or heating and the pH of the reaction was continuously monitored. The pH dropped dramatically from 11 and leveled off around 8.5. Upon finishing the addition, the feed port and line were rinsed with 3 grams of distilled water. The reaction mixture was then held at from 60° C. to 63° C. for about 30 minutes. The pH drop to a minimum of about 8 and then started to increase. 0.60 grams of 25% NaOH were added to the reaction flask and the temperature was held at from 60° C. to 63° C. and pH was monitored until it was above 9 and constant.

Example 2

A copolymer wherein one or more monomeric units of the polymer each comprise two quaternary ammonium groups per monomeric unit was made according to Scheme C-1:

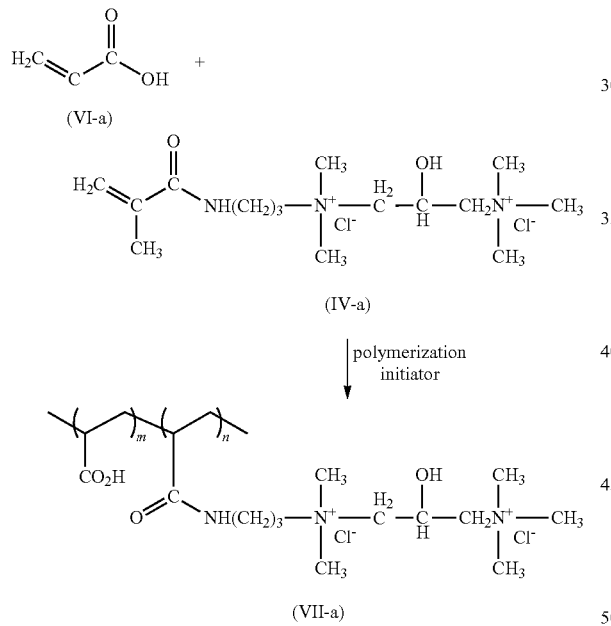

by reacting acrylic acid (VI-a) with a di-quaternary monomer (IV-a) made according to Example 1 to form the copolymer (VII-a) having first monomeric units derived from the di-quaternary monomer and second monomeric units derived from acrylic acid, wherein m is an integer of from 800 to 6,000 and n is an integer of from 400 to 3,000.

To a one-liter flask equipped with a condenser, a mechanic stirrer, a thermo-couple and a gas inlet was added 52.1 g acrylic acid (BASF), 193.4 g di-quaternary monomer made according to Example 1, and 593.9 g distilled water. The content was heated to a temperature in the range of from 70° C. to 72° C. under mixing and nitrogen sparging. Stirring and nitrogen sparging was maintained throughout the reaction. After the content was sparged for 1 hour, sodium persulfate 0.094 g in 2 ml of water was added. An exothermic reaction began, and cooling or heating was applied to maintain temperature in a range of from 70 to 72° C. After 2 hours of reaction, sodium metabisulfite 0.23 g in 1 ml of water was added. The batch temperature was gradually reduced to from 63 to 65° C. over 1 hour. Then sodium metabisulfite 0.40 g in 2 ml of water was added and followed by sodium persulfate 0.08 g in 1 ml of water and the temperature of the batch was held at from 63° C. to 65° C. for 1 hour. The last step was repeated until non-reacted residual monomers were less than 10 ppm.

The invention claimed is:

1. A method for making a monomer having an ethylenically unsaturated group and two or more quaternary ammonium groups per molecule, comprising:
   (a) reacting an excess of a monomeric reactant having at least one ethylenically unsaturated group and at least one tertiary amino group per molecule with a halohydroxyalkyl(trialkyl)quaternary ammonium salt, in an aqueous medium,
   (b) monitoring the pH of the aqueous medium from at least as early as the time when all reactants have been added to aqueous medium until completion of the reaction, and
   (c) adjusting the pH of the aqueous medium to and maintaining the pH of the aqueous medium at a value greater than or equal to 9, from the time, after all reactants have been added to aqueous medium, that the reaction mixture exhibits an apparent pH minimum until completion of the reaction.

2. A method according to claim 1, wherein a monomer (IV) is made according to Scheme A:

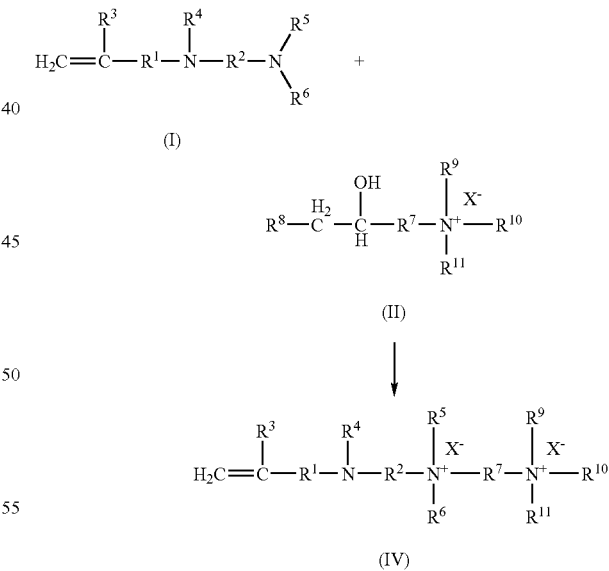

by reacting an excess of a monomer according to structure (I), wherein:
   $R^1$ is a divalent organic linking group, which may optionally be substituted on one or more carbon atoms or interrupted at one or more sites by heteroatoms,
   $R^2$ is alkylene, which may optionally be substituted on one or more carbon atoms or interrupted at one or more sites by heteroatoms, or a group according to:

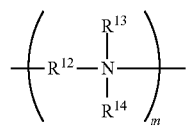

wherein
- $R^{12}$ is alkylene, which may optionally be substituted on one or more carbon atoms or interrupted at one or more sites by heteroatoms,
- $R^{13}$ and $R^{14}$ are each independently alkyl, and m is an integer of from 1 to 6,
- $R^3$ is H or $(C_1-C_6)$alkyl,
- $R^4$ is H or $(C_1-C_6)$alkyl,
- $R^5$ and $R^6$ are each independently $(C_1-C_6)$alkyl, with a haloalkyl(trialkyl)quaternary ammonium salt according to structure (II), wherein:
- $R^7$ is a divalent organic linking group,
- $R^8$ is halo,
- $R^9$, $R^{10}$ and $R^{11}$ are each independently alkyl, and
- $X^-$ is an anion.

3. A method according to claim 1, wherein a monomer (IV-a) is made according to Scheme A-1:

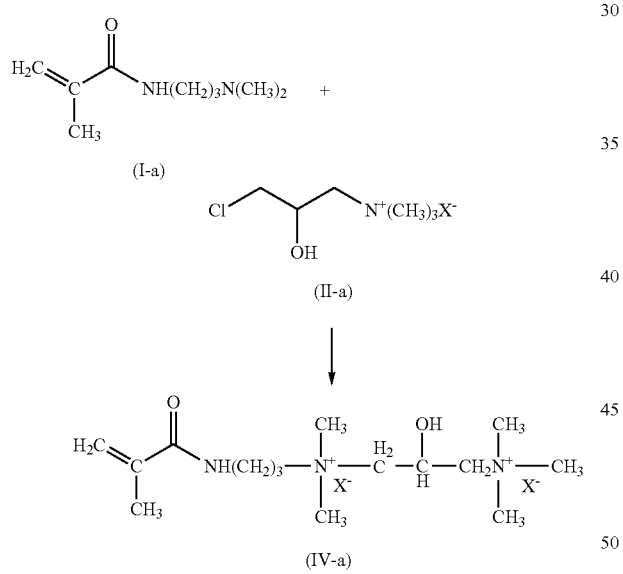

by reacting an excess of a monomer (I-a) with a haloalkyl (trialkyl)quaternary ammonium salt (II-a) wherein $R^8$ is halo and $X^-$ is an anion.

4. The method of claim 3, wherein $R^8$ is chloro and X— is $Cl^-$.

5. A process for making a polymer wherein one or more monomeric units of the polymer each comprise two or more quaternary ammonium groups per monomeric unit, comprising:
(a) making a monomer having an ethylenically unsaturated group and two or more quaternary ammonium groups per molecule by:
(i) reacting an excess of a monomer having at least one ethylenically unsaturated group and at least one tertiary amino group per molecule with a halohydroxy-alkyl(trialkyl)quaternary ammonium salt in an aqueous medium,
(ii) monitoring the pH of the aqueous medium from at least as early as the time when all reactants have been added to aqueous medium until completion of the reaction, and
(iii) adjusting the pH of the aqueous medium to and maintaining the pH of the aqueous medium at a value greater than or equal to 9, from the time after all reactants have been added to aqueous medium, that the reaction mixture exhibits an apparent pH minimum until completion of the reaction, and
(b) polymerizing the monomer formed in step (a) in the presence of a polymerization initiator mixture.

6. The method of claim 5, wherein the polymer is made according to Scheme B:

Scheme B

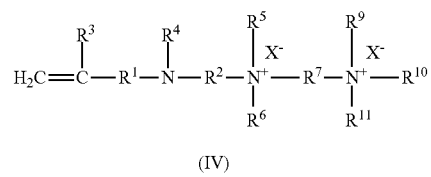

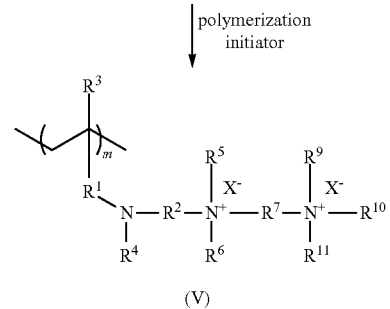

by polymerizing a monomer according to structure (IV), wherein
- $R^1$ is a divalent organic linking group, which may optionally be substituted on one or more carbon atoms or interrupted at one or more sites by heteroatoms,
- $R^2$ is alkylene, which may optionally be substituted on one or more carbon atoms or interrupted at one or more sites by heteroatoms, or a group according to:

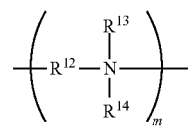

wherein
- $R^{12}$ is alkylene, which may optionally be substituted on one or more carbon atoms or interrupted at one or more sites by heteroatoms,
- $R^{13}$ and $R^{14}$ are each independently alkyl, and m is an integer of from 1 to 6,
- $R^3$ is H or $(C_1-C_6)$alkyl,
- $R^4$ is H or $(C_1-C_6)$alkyl,
- $R^5$ and $R^6$ are each independently $(C_1-C_6)$alkyl,
- $R^7$ is a divalent organic linking group, R$^8$ is halo,
R$^9$, R$^{10}$ and R$^{11}$ are each independently alkyl, and
X$^-$ is an anion
in the presence of a polymerization initiator to form a homopolymer according to structure (V), wherein m is an integer of from 2 to about 30,000.

7. The method of claim 5, wherein the polymer is made according to Scheme C:

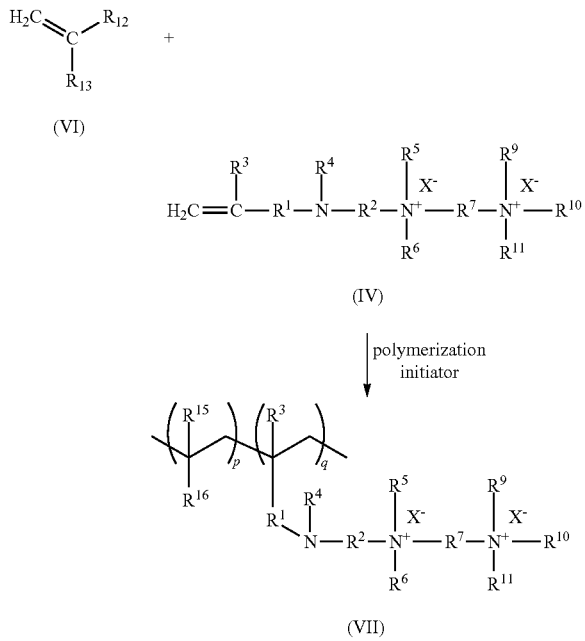

by copolymerizing a monomer according to structure (IV), wherein

R$^1$ is a divalent organic linking group, which may optionally be substituted on one or more carbon atoms or interrupted at one or more sites by heteroatoms, R$^2$ is alkylene, which may optionally be substituted on one or more carbon atoms or interrupted at one or more sites by heteroatoms, or a group according to:

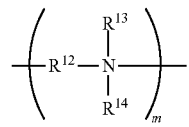

wherein:
R$^{12}$ is alkylene, which may optionally be substituted on one or more carbon atoms or interrupted at one or more sites by heteroatoms,
R$^{13}$ and R$^{14}$ are each independently alkyl, and
m is an integer of from 1 to 6,
R$^3$ is H or (C$_1$-C$_6$)alkyl,
R$^4$ is H or (C$_1$-C$_6$)alkyl,
R$^5$ and R$^6$ are each independently (C$_1$-C$_6$)alkyl,
R$^7$ is a divalent organic linking group,
R$^8$ is halo,
R$^9$, R$^{10}$ and R$^{11}$ are each independently alkyl, and
X$^-$ is an anion,
with a co-monomer (VI), wherein:
R$^{15}$ is H or (C$_1$-C$_6$)alkyl, and
R$^{16}$ is hydroxyl,
in the presence of a polymerization initiator to form a copolymer according to structure (VII), wherein p and q are each integers of from 1 to about 100,000.

8. The method of claim 7, wherein a polymer (VII-a) is made according to Scheme C-1:

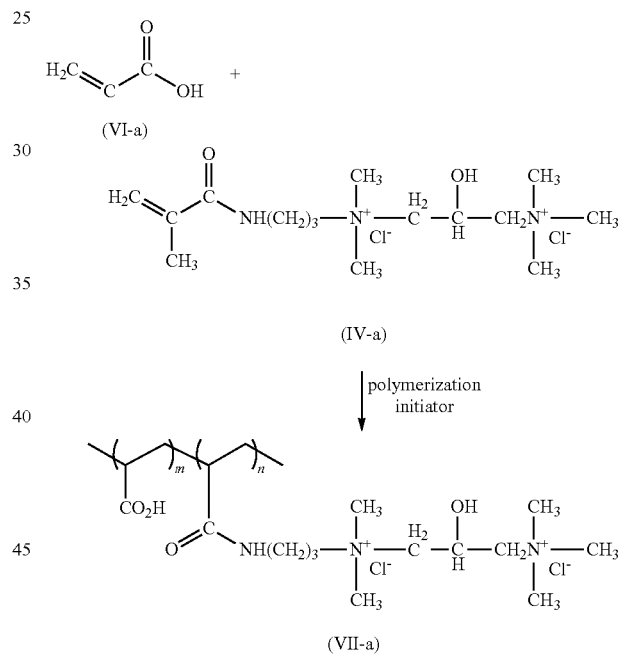

by reacting acrylic acid (VI-a) with a di-quaternary monomer (IV-a), wherein X— is an anion and wherein m is an integer of from about 800 to 6,000 and n is an integer of from about 400 to 3,000.

9. The method of claim 8, wherein X— is Cl$^-$.

* * * * *